United States Patent
Olson et al.

(10) Patent No.: US 10,350,385 B2
(45) Date of Patent: Jul. 16, 2019

(54) THERMODILUTION CATHETER

(71) Applicant: Regents of the University of Minnesota, Minneapolis, MN (US)

(72) Inventors: Matthew D. Olson, Eagan, MN (US); Demetris Yannopoulos, Edina, MN (US); Jason Bartos, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 42 days.

(21) Appl. No.: 15/602,733

(22) Filed: May 23, 2017

(65) Prior Publication Data
US 2017/0333671 A1    Nov. 23, 2017

Related U.S. Application Data

(60) Provisional application No. 62/340,230, filed on May 23, 2016.

(51) Int. Cl.
| | |
|---|---|
| *A61M 25/00* | (2006.01) |
| *A61B 5/028* | (2006.01) |
| *A61B 5/029* | (2006.01) |
| *A61M 25/10* | (2013.01) |
| *A61M 29/02* | (2006.01) |
| *A61M 25/09* | (2006.01) |

(Continued)

(52) U.S. Cl.
CPC ............ *A61M 25/007* (2013.01); *A61B 5/01* (2013.01); *A61B 5/028* (2013.01); *A61B 5/029* (2013.01); *A61B 5/6853* (2013.01); *A61M 25/09* (2013.01); *A61M 25/10* (2013.01); *A61M 29/02* (2013.01); *A61M 2025/0004* (2013.01); *A61M 2230/04* (2013.01); *A61M 2230/50* (2013.01)

(58) Field of Classification Search
CPC ....... A61M 25/007; A61B 5/028; A61B 5/029
See application file for complete search history.

(56) References Cited

U.S. PATENT DOCUMENTS

| | | | | |
|---|---|---|---|---|
| 3,726,269 A | * | 4/1973 | Webster, Jr. ........... | A61B 5/028 600/526 |
| 4,733,669 A | * | 3/1988 | Segal ................... | A61B 5/6886 600/465 |

(Continued)

*Primary Examiner* — William J Levicky
(74) *Attorney, Agent, or Firm* — Schwegman Lundberg & Woessner, P.A.

(57) ABSTRACT

A system includes an outer catheter and an inner catheter. The outer catheter has a proximal end and a distal end. The distal end has a discharge nozzle, a tapered interior wall, and an end orifice. The proximal end is configured to receive a fluid. The discharge nozzle is coupled to the proximal end by a first lumen. The discharge nozzle is configured to direct the fluid in a plurality of discrete streams aligned in a radial fashion about an axis of the first lumen. The interior catheter is configured for placement within the first lumen. A first end of the interior catheter includes an occluder and includes a first temperature sensor. The first temperature sensor is configured to pass through the end orifice. The occluder is configured to engage with the tapered interior wall in a fluid-tight seal. The first temperature sensor includes a sense surface and includes a signal node. The signal node is configured to provide a first signal corresponding to a timewise change in temperature at the sense surface.

34 Claims, 4 Drawing Sheets

(51) Int. Cl.
*A61B 5/00* (2006.01)
*A61B 5/01* (2006.01)

(56) References Cited

U.S. PATENT DOCUMENTS

| | | | |
|---|---|---|---|
| 5,009,234 A * | 4/1991 | Alt | A61B 5/028 600/485 |
| 6,089,103 A * | 7/2000 | Smith | A61B 5/028 600/486 |
| 8,016,766 B2 | 9/2011 | Goedje et al. | |
| 2005/0101920 A1* | 5/2005 | Keane | A61B 5/15003 604/218 |
| 2008/0076960 A1* | 3/2008 | Marseille | A61M 25/04 600/16 |
| 2009/0137917 A1 | 5/2009 | Goedje et al. | |

* cited by examiner

THERMODILUTION CATHETER

CLAIM OF PRIORITY

This patent application claims the benefit of priority of U.S. Provisional Patent Application Ser. No. 62/340,230 filed on 23 May 2016, which is hereby incorporated by reference herein in its entirety.

BACKGROUND

Cardiac output is a physiological parameter and can be expressed as a product of heart rate and stroke volume. Cardiac output can be measured by using a catheter to introduce saline in the pulmonary artery or right ventricular outflow tract and measuring a downstream temperature change.

One such approach, known as thermodilution uses a biased thermistor located at the tip of a multi-lumen balloon tipped catheter that is transvenously advanced into the right atrium, ventricle, and ultimately into the pulmonary artery. At which point, an indicator solution (such as normal saline) is injected into one of the lumens with the end-hole of the catheter positioned within the right atrium. The change in temperature is measured at the distal thermistor during and shortly after the completion of a hand injection procedure. This dilution is then integrated and a cardiac output is calculated. The method is based upon the Stewart-Hamilton equation.

Inaccuracies in measured cardiac output can be related to atypical anatomy, low blood flow states, and during times of advanced circulatory support such as extracorporeal membrane oxygenation (ECMO), and severe tricuspid regurgitation back into the atrium.

U.S. Pat. No. 8,016,766 refers to a central venous catheter assembly for measuring physiological data for cardiac output determination and a method of determining cardiac output.

SUMMARY

An example of the present subject matter includes an injector nozzle configured to form a mixing cloud proximate the distal end of a catheter. The injector nozzle can include multiple holes in a sidewall of a catheter. The holes can be formed by a laser drilling process.

Fluid is discharged from the injector nozzle of the present subject matter in a plurality of radial directions relative to the longitudinal axis of the catheter. The radially discharged fluid tends to force the body of the catheter towards the center of the lumen. With the catheter positioned near the center of the lumen, the fluid is more uniformly or fully distributed. Uniform fluid distribution can lead to improved mixing and thus, can enable measurement of the thermal profile over a relatively short distance.

A relatively short distance can reduce or eliminate the effects of significant tricuspid regurgitation. In one example, the present subject matter allows cardiac output to be measured accurately in settings in conjunction with parallel flow circuits (advanced circulatory support) such as ECMO, LVAD, and right heart augmentation devices. In one example, the present subject matter facilitates evaluating the efficacy of cardiac output during percutaneous pulmonic valve implantation. In one example, measuring output through the pulmonary artery allows for accurate measurement using shunt fractions, particularly right to left shunts. In one example, a system is configured with dimensions to allow placement within a coronary artery in which a diluent can be injected to measure flow in a manner analogous to cardiac output.

One example of the present subject matter includes a catheter configured for measuring cardiac output using thermodilution using a novel mixing approach and microthermocouples with rapid time constants.

A problem associated with currently available approaches to cardiac output measurement uses a relatively lengthy coil and determines the changes in temperature as blood flows past the coil. Other techniques rely on measuring venous and arterial gases, evaluating impedance changes, and injecting perfectly cooled saline. These approaches do not provide a compact device for accurate measurement of cardiac output.

One example of the present subject matter includes a catheter having a discharge nozzle, sometimes called an injector nozzle, and a temperature sensor in a compact assembly that enables cardiac output measurement over a dimension that fits wholly within the main pulmonary artery, distal right ventricular outflow tract, or proximal section of the right or left pulmonary arteries. An example of the present subject matter allows for measuring blood passing through the pulmonary circulation, and thus omits the need for a right atrial mixing chamber.

Each of these non-limiting examples can stand on its own, or can be combined in various permutations or combinations with one or more of the other examples.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
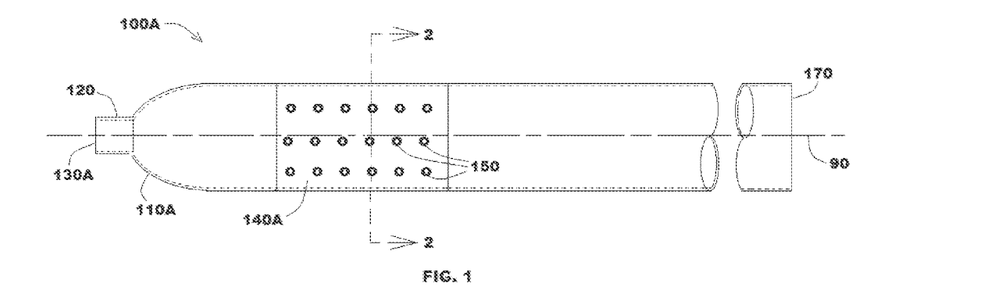
FIG. 1 illustrates an outer catheter, according to one example.

FIG. 1 illustrates outer catheter 100A, according to one example. Outer catheter 100A includes a single or multi-lumen catheter having proximal end 170 and distal end 110A terminating with orifice 130A. In the example shown, orifice 130A is disposed on stub end 120. Distal end 110A has a rounded profile, and in the example shown, the wall thickness is relatively uniform and as such, the interior wall of outer catheter 100A includes a rounded profile.

Outer catheter 100A includes discharge nozzle 140A proximate distal end 110A. Discharge nozzle 140A includes a plurality of orifices 150 distributed radially with respect to longitudinal axis 90. Longitudinal axis 90 is aligned between proximal end 170 and distal end 110A.

Outer catheter 100A can be fabricated of a nylon-based moldable plastic such as a polyether block amide (an example of which includes Pebax). In one example, the distal end 110A has a tapered profile. In one example, stub end 120 has a diameter of approximately 0.040 inches.

Outer catheter 100A can have multiple lumens, including, for example, a lumen coupled to a proximal-end saline injection port (not shown). In one example, the proximal-end saline injection port is a side hole positioned approximately 30 cm from the discharge nozzle 140A.

Figure 2:
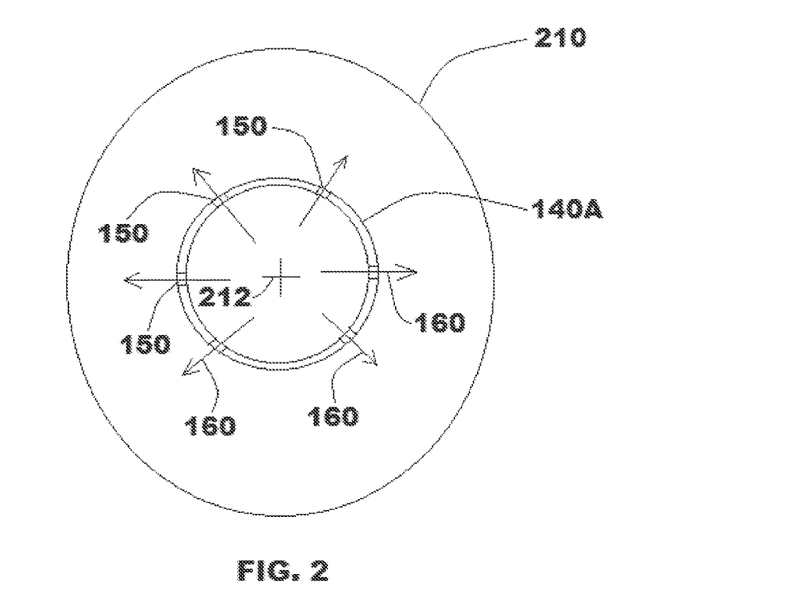
FIG. 2 illustrates a view of an outer catheter, according to one example.

FIG. 2 illustrates an end view of discharge nozzle 140A, according to one example. The view illustrated in FIG. 2 is taken along the cut line marked with arrows 2 in FIG. 1. Discharge nozzle 140A, in the example shown, includes six rows of orifices, some orifices of which are marked orifice 150 and are arranged radially about axis 90, here denoted with cross-hairs 212. In other examples, a plurality of orifices are arranged in a random pattern or an ordered pattern (such as rows of any number from two to 50) with the number of orifices limited by the dimensions of the nozzle and the diameter of the orifices. Each orifice 150 is configured to discharge a fluid in a radial direction, and in the figure, the fluid discharge streams are denoted as stream 160.

The fluid discharged via the orifices 150 will tend to center the nozzle 140A within the interior region of tract 210. Tract 210 can represent a main pulmonary artery, a distal right ventricular outflow tract, a section of the right or left pulmonary arteries, or other body cavity (such as the coronary or cerebral arterial circulation).

An orifice 150 can include a hole having a diameter of approximately 0.004 inches. In one example, discharge nozzle 140A includes six rows of holes with each row having seven holes and evenly distributed over the circumference of the outer catheter 100A. In one example, each row has a length of approximately 0.20 inches. In one example, discharge nozzle 140A includes a laser-drilled body of Pebax having a durometer of 72 shore A.

Figure 3:
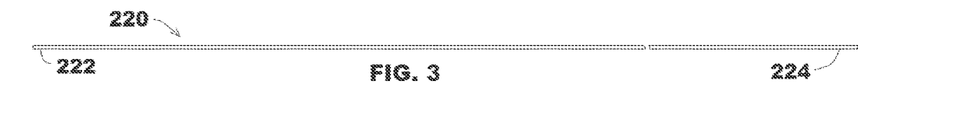
FIG. 3 illustrates a guide wire, according to one example.

FIG. 3 illustrates a view of guide wire 220, according to one example. Guide wire 220 includes a distal end 222 and proximal end 224. Guide wire 220 can includes any combination of rigid or flexible wire and can be maneuvered to lie within an arterial passage of a patient. Guide wire 220 can provide a guide for later placement of outer catheter 100A. In one example, guide wire 220 is implanted in a patient and outer catheter 100A is maneuvered to pass orifice 130A over proximal end 224 and in a direction to bring orifice 130A toward distal end 222. Outer catheter 100A is maneuvered to position discharge nozzle 140A at a particular location within the patient. With discharge nozzle 140A located in the particular location, guide wire 220 can be extracted by withdrawing from distal end 170 of outer catheter 100A.

Guide wire 220 can include a plain guide wire (having, for example, a diameter of 0.035" diameter). Guide wire 220 can sometimes be referred to as a Swan wire.

Guide wire 220 can by positioned within a through-lumen of an outer catheter, such as outer catheter 100A. A through-lumen can extend from the distal end 110A (at orifice 130A, for example) through a central injection port that can accept a standard Swan wire. The through-lumen, the guide wire, or both the lumen and the wire, can be coated with a lubricant or can include a surface treated with a lubricant, such as polytetrafluoroethylene (PTFE). A Tuohy (not shown) can be coupled to the through-lumen to enable both the inner catheter body 330 (FIG. 6, for example) and saline injections to occupy the same space.

Figure 4:
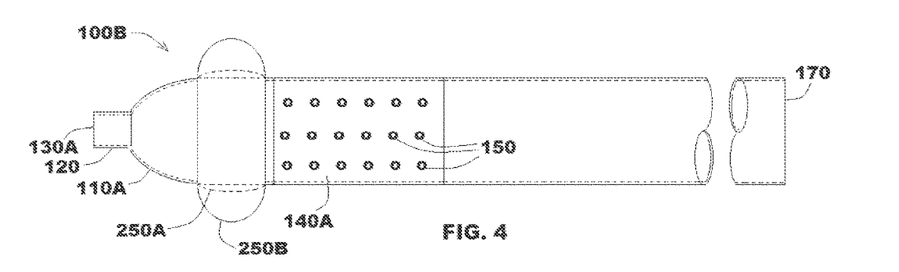
FIG. 4 illustrates an outer catheter, according to one example.

FIG. 4 illustrates outer catheter 100B, according to one example. In the example shown, catheter 100B includes inflated balloon 250B disposed near distal end 110A. Deflated balloon 250A illustrates a configuration at a time before balloon 250B is inflated. Outer catheter 100B can be positioned within a patient vessel or tract by a process sometimes referred to as floating. In a floating operation, balloon 250B presents a resistance to arterial flow and, when inflated as shown in the figure, the balloon 250B (along with outer catheter 100B, discharge nozzle 140A, and proximal end 170), are maneuvered within a direction of the blood flow. The blood flow carries distal end 110A of outer catheter 100B to a particular location. After positioning outer catheter 100B, balloon 250B is deflated as shown at balloon 250A. In use, the injected fluid emitted from orifices 150 is mixed with the blood flow in the vicinity of discharge nozzle 140A.

Balloon 250B can be coupled to a balloon inflation port located proximate distal end 170 by a balloon inflation lumen.

In one example, outer catheter 100B is configured with a through-lumen having a lining of PTFE (such as Teflon) lining. The proximal 100 cm of the outer catheter 100B includes Pebax having a durometer of 72 and the distal 15 cm includes Pebax having a durometer of 55. In one example, the outer catheter 100B is sized to accommodate a 6F system. In one example, outer catheter 100B includes a vascular access sheath and an assembly including a PTFE liner, a Pebax outer jacket, and a cross-linked PFE heat shrink tubing. One example includes a metallic or polymer support braid encased in a Pebax outer jacket that is fused to inner materials with cross-linked PFE heat shrink tubing. The outer diameter goal is to be compatible with a 5F or 6F system. The materials, hardness, and dimensions can be tailored to suit a particular application.

Figure 5:
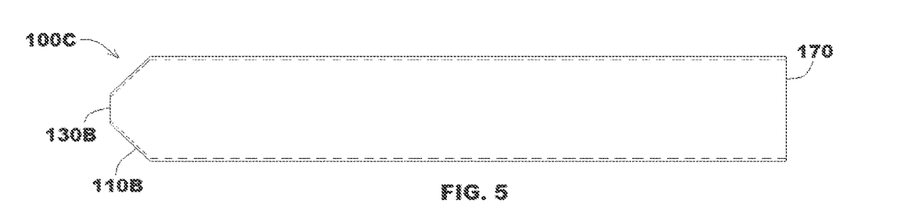
FIG. 5 illustrates an outer catheter, according to one example.

FIG. 5 illustrates outer catheter 100C, according to one example. Outer catheter 100C includes distal end 110B configured with a tapered profile. Outer catheter 100C includes orifice 130B and, in the example shown, omits a stub end or extension. Outer catheter 100C includes a discharge nozzle (not shown in this view) disposed near distal end 110B and remote from distal end 170. Outer catheter 100C can be positioned in a patient using a guide wire, such as guide wire 220, can be positioned by a balloon (such as balloon 250B; not shown in this view) and floating, or can be positioned by other means.

Proximal end 170 can be configured to engage a handle. The handle (not shown) can provide fluid couplings and can provide electrical connectors for interfacing with a remote device suited for support or monitoring.

Figure 6:
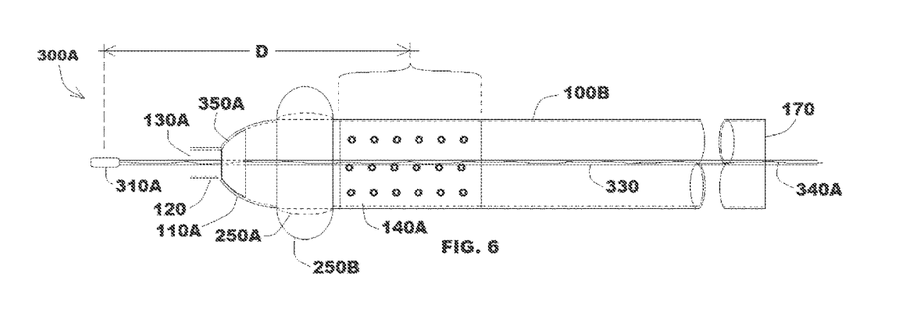
FIG. 6 illustrates a portion of a thermodilution system, according to one example.

FIG. 6 illustrates a portion of thermodilution system 300A, according to one example. System 300A includes outer catheter 100B having discharge nozzle 140A and balloon 250B (balloon 250A shown in deflated configuration) proximate distal end 110A. Outer catheter 100B includes proximal end 170 and includes distal end 110A having stub end 120 and orifice 130A.

Inner catheter body 330 is coupled to temperature sensor 310A at a distal end. Temperature sensor 310A is configured to provide an output signal on node 340A based on a temperature sensed at a surface of sensor 310A. Temperature sensor 310A can include a thermistor, thermocouple, or other temperature sensor, and in one example, provides a microvoltage output signal. The output signal can be determined by a temperature or a temperature change. Inner catheter body 330 is coupled to plug 350A (sometimes called occluder 350A) having a contour configured to provide a fluid-tight seal on an interior surface of outer catheter 100B and thereby prevent fluid discharge from orifice 130A. Plug 350A, in the example shown, includes a rounded profile. With plug 350A configured to occlude orifice 130A, fluid introduced at proximal end 170 will discharge through discharge nozzle 140A. Plug 350A can also have a contoured profile on the proximal side. A contoured profile on the proximal side can reduce friction and can improve ease of removal from the outer catheter 100B.

Temperature sensor 310A is configured to pass through orifice 130A. Temperature sensor 310A is spaced apart from discharge nozzle 140A by dimension D. Dimension D is selected to provide a compact system 300A and to provide a measure of temperature at a location near the fluid introduction via nozzle 140A.

One operation entails sliding the inner catheter body 330 into the outer catheter until the plug 350A occludes and prevents discharge from the end orifice 130A.

In one example, temperature sensor 310A is a type T microthermocouple. In one example, temperature sensor 310A is fitted with a j-shaped tip wire.

Figure 7:
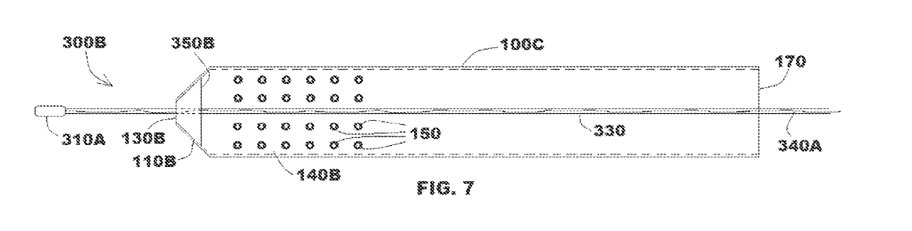
FIG. 7 illustrates a portion of a thermodilution system, according to one example.

FIG. 7 illustrates a portion of a thermodilution system 300B, according to one example. In the figure, inner catheter body 330 is coupled to plug 350B. Plug 350B includes a faceted sealing profile configured to engage the profile of an interior surface of outer catheter 100C corresponding to distal end 110B. Plug 350B is configured to occlude fluid passage through orifice 130B. With plug 350B configured to occlude orifice 130B, fluid introduced at proximal end 170 will discharge through discharge nozzle 140B via orifices 150. Temperature sensor 310A is configured to pass through orifice 130B and provide an output signal on node 340A based on a sensed temperature.

Figure 8A:
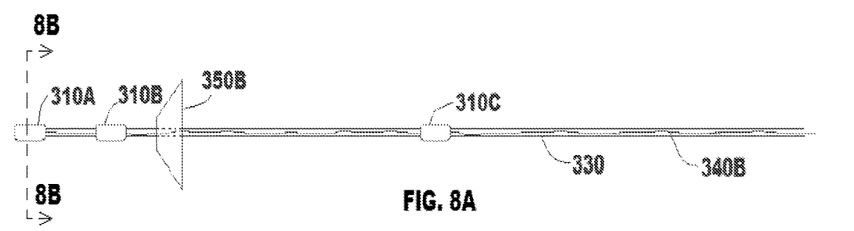
FIG. 8A illustrates an inner catheter, according to one example.

FIG. 8A illustrates inner catheter body 330, according to one example. In the example shown, inner catheter body 330 is coupled to temperature sensor 310A, temperature sensor 310B, and temperature sensor 310C, as well as plug 350B. Temperature sensor 310A, sometimes referred to as a first thermistor, is positioned at a distal end of body 330 and provides a measure of temperature near, for example, distal end 110B. In addition, temperature sensor 310B, sometimes referred to as a second thermistor, provides a measure of temperature at a fixed dimension relative to the position of temperature sensor 310A. In addition, temperature sensor 310C, sometimes referred to as a third thermistor, is configured to provide a measure of temperature within a lumen of outer catheter 100A, for example, and before discharge via discharge nozzle 140A. Plug 350B is configured to occlude an orifice of outer catheter 100A, for example.

Plug 350B can include an elastic portion or a Pebax bulge that functions to limit the travel of inner catheter body 330 and functions as a plug or gasket during fluid injection. Plug 350B occludes orifice 130B and forces injected fluid out of the side holes of the discharge nozzle 140B.

Inner catheter body 330 is coupled to one or more temperature sensors. The temperature sensors, some examples of which include sensor 310A, 310B, and 310C can include a cylindrical sensor having a sense surface on a cylindrical wall or on an end wall, and are configured to provide output signals on node 340B.

In one example, temperature sensor 310A, 310B, or 310C are electrically coupled by spot welded or soldered electrical conductors and are fitted within a jacket of Pebax or other material.

Temperature sensors 310A, 310B, or 310C are located at positions along the length of body 330 such that thermodilution calculations based on the measured temperatures can provide a measure of cardiac output. For example, one temperature sensor can be positioned just proximal to discharge nozzle 140A and other temperature sensors can be positioned at 3 cm and 4.5 cm distal to discharge nozzle 140A.

Inner catheter body 330 is coupled to a plug configured to occlude an outer discharge port on the outer catheter.

Figure 8B:
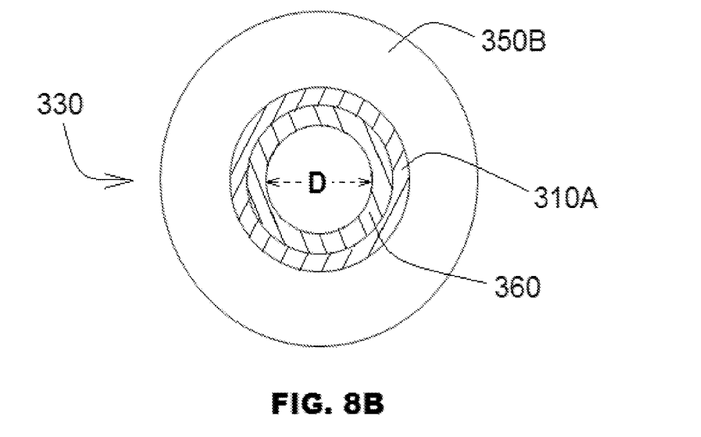
FIG. 8B illustrates a cross-sectional view of a catheter, according to one example.

FIG. 8B illustrates a cross-sectional view of catheter 330, according to one example. In the view shown, catheter 330 includes an internal sleeve 360. Inner sleeve 360 extends along the length and allows passage of a coronary or cerebral guidewire. In various examples, inner sleeve 360 includes a lining of PTFE or of polyimide. In one example, the present subject matter is suitable for measuring differences in blood flow (cardiac output) within smaller arterial or venous vascular beds. Inner sleeve 360 has a lumen of diameter D. In one example, diameter D has a dimension of 0.018 inches however, other dimensions are also contemplated. A guide wire suitable for use in one example has a diameter of 0.014 inches. Sensor 310A and plug 350B are visible in the image shown.

Figure 9A:
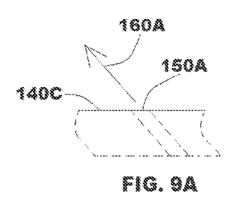
FIGS. 9A, 9B, and 9C each illustrate a portion of a discharge nozzle.
Figure 9B:
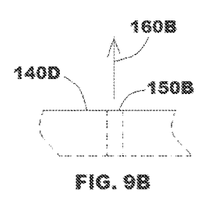
Figure 9C:
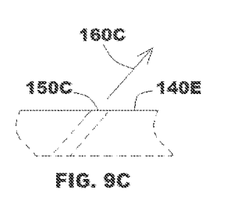

FIGS. 9A, 9B, and 9C each illustrate a portion of a discharge nozzle. At FIG. 9A, discharge nozzle 140C illustrates aperture 150A having an angular alignment which is configured to discharge fluid in an antegrade direction as shown by discharge stream 160A.

At FIG. 9B, discharge nozzle 140D illustrates aperture 150B having an angular alignment which is configured to discharge fluid in a direction relatively normal to axis, such as axis 90, and along a discharge stream 160B.

At FIG. 9C, discharge nozzle 140E illustrates aperture 150C having an angular alignment which is configured to discharge fluid in a retrograde direction relative to axis, such as axis 90, and along a discharge stream 160C.

Figure 10:
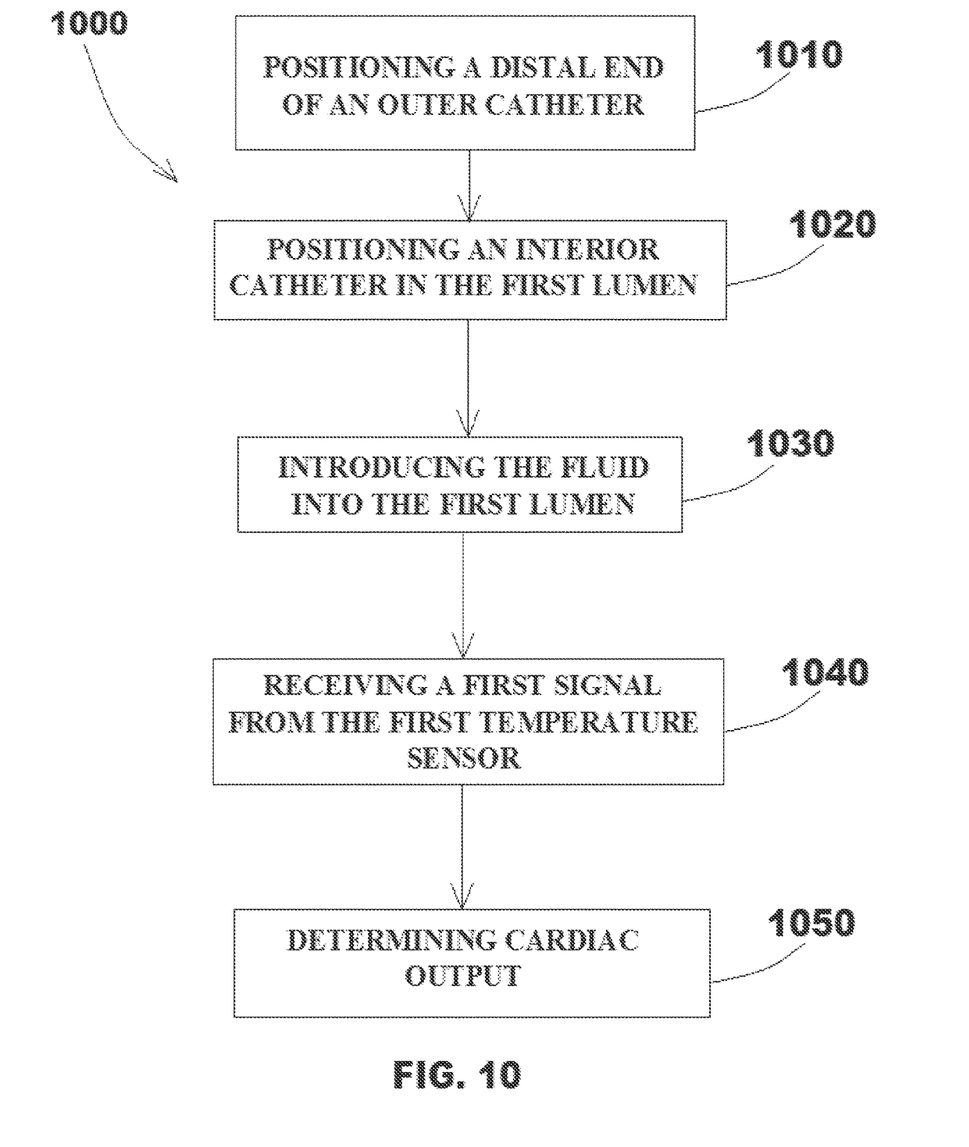
FIG. 10 illustrates a method, according to one example.

FIG. 10 illustrates method 1000, according to one example. At 1010, method 1000 includes positioning a distal end of an outer catheter at a target location. The target location can be within a main pulmonary artery. Placement of the distal end can include positioning the discharge nozzle at a selected location. Positioning the distal end can include using a guidewire for placement or can include using a balloon and a floating procedure.

At 1020, method 1000 includes positioning an interior catheter within a first lumen of the outer catheter. This can include passing a first temperature sensor (such as a thermistor), through the proximal end (such as end 170), through the orifice 130A, and forming a fluid-tight seal at to occlude discharge from orifice 130A by engaging a plug and an interior wall section of outer catheter.

At 1030, method 1000 includes introducing an injection fluid into the first lumen of the outer catheter. Introducing the fluid can include using a manually syringe or pump to introduce fluid.

At 1040, method 1000 includes receiving a first signal from the first temperature sensor. The first signal can include a timewise representation of a temperature.

At 1050, method 1000 includes determining cardiac output based on the measured temperature at the first temperature sensor. A computer implemented program can be configured to calculate a measure of cardiac output. For example, a program such as LABVIEW can be configured for such use.

Variations of the above method are also contemplated. For example, a second guide wire, such as 0.014 inch or smaller, can be inserted through a lumen of catheter 330. For example, this configuration allows for over the wire advance into a smaller vessel bed. In one example, such as at 1020 of method 1000, the guide wire allows for placement of the catheter in a smaller vessel bed. The guide wire can include a coronary or cerebral guidewire.

One aspect of some examples of the present subject matter includes formation of a fluid mixing cloud formed by the multiple apertures at the distal end of the outer catheter. The apertures can be laser-formed. The configuration of apertures can be tailored to force the outer catheter to approach the center of the body cavity, thus fully distributing the inject fluid (such as cold saline) in many directions, thus improving mixing efficiency and thus reducing the distance needed to measure cardiac output. A shortened distance mitigates several problems with the current thermodilution techniques.

In one example, mixing of the injected fluid and the blood occurs within the pulmonary artery.

Various Notes

An example of the present subject matter can be configured for use with a critically ill cardiac patient receiving ECMO therapy or another form of hemodynamic support, has very low cardiac output, has a significant shunt, has significant tricuspid regurgitation, or is undergoing pulmonary valve implant through percutaneous means.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system comprising:
   an outer catheter having a proximal end and a distal end, the distal end having a discharge nozzle, a tapered interior wall, and an end orifice, the proximal end configured to receive a fluid, the discharge nozzle coupled to the proximal end by a first lumen, the discharge nozzle configured to direct the fluid in a plurality of discrete streams aligned in a radial fashion about an axis of the first lumen;
   an interior catheter configured for placement within the first lumen, wherein a first end of the interior catheter includes an occluder and includes a first temperature sensor, the first temperature sensor configured to pass through the end orifice and the occluder configured to engage with the tapered interior wall in a fluid-tight seal;
   wherein the first temperature sensor includes a sense surface and includes a signal node, wherein the signal node is configured to provide a first signal corresponding to a timewise change in temperature at the sense surface; and
   wherein the interior catheter includes a second temperature sensor distal from the occluder and wherein a second signal from the second temperature sensor corresponds to a timewise chance in temperature.

2. The system of claim 1 further including a guide wire configured to facilitate placement of the outer catheter, the guide wire configured to pass through the end orifice and the guide wire configured for extraction from the first lumen at the proximal end.

3. The system of claim 1 wherein the distal end of the outer catheter includes a balloon, the balloon configured for inflation by a second lumen, the second lumen having a first end coupled to an interior region of the balloon and having a second end proximate the proximal.

4. The system of claim 1 wherein the occluder includes an elastic portion.

5. The system of claim 1 wherein the discharge nozzle includes a plurality of apertures, wherein each aperture corresponds to a discrete stream.

6. The system of claim 5 wherein at least one aperture is aligned in a retrograde direction.

7. The system of claim 5 wherein at least one aperture is aligned in an antegrade direction.

8. The system of claim 5 wherein at least one aperture is aligned perpendicular to the axis.

9. A method of determining cardiac output comprising:
positioning a distal end of an outer catheter in a blood tract, the distal end having a discharge nozzle, a tapered interior wall, and an end orifice, the outer catheter having a proximal end configured to receive a fluid, the discharge nozzle coupled to the proximal end by a first lumen;
positioning an interior catheter in the first lumen, wherein a first end of the interior catheter includes an occluder and includes a first temperature sensor, the first temperature sensor configured to pass through the end orifice and the occluder configured to engage with the tapered interior wall in a fluid-tight seal;
introducing the fluid into the first lumen at the proximal end and discharging the fluid from the first lumen at the discharge nozzle, wherein discharging the fluid includes directing the fluid in a plurality of discrete streams aligned in a radial fashion about an axis of the first lumen;
receiving a first signal from the first temperature sensor, the first signal corresponding to a timewise change in temperature;
determining cardiac output using the first signal; and
wherein positioning the interior catheter includes positioning a second temperature sensor distal from the occluder and further including receiving a second signal from the second temperature sensor, the second signal corresponding to a timewise change in temperature.

10. The method of claim 9 wherein positioning the distal end of the outer catheter includes passing the outer catheter over a guide wire.

11. The method of claim 9 further including extracting the guide wire from the first lumen at the proximal end.

12. The method of claim 9 wherein positioning the distal end of the outer catheter includes inflating a balloon and deflating the balloon, the balloon coupled to the distal end.

13. The method of claim 9 wherein positioning the interior catheter includes deforming an elastic portion of the occluder.

14. The method of claim 9 wherein discharging the fluid from the first lumen at the discharge nozzle includes discharging the fluid in a discrete stream aligned in a retrograde direction.

15. The method of claim 9 wherein discharging he fluid from the first lumen at the discharge nozzle includes discharging the fluid in a discrete stream aligned in an antegrade direction.

16. The method of claim 9 wherein discharging the fluid from the first lumen at the discharge nozzle includes discharging the fluid in a discrete stream aligned perpendicular to the axis.

17. The method of claim 9 wherein positioning the interior catheter includes advancing over a guidewire.

18. A system comprising:
an outer catheter having a proximal end and a distal end, the distal end having a discharge nozzle, a tapered interior wall, and an end orifice, the proximal end configured to receive a fluid, the discharge nozzle coupled to the proximal end by a first lumen, the discharge nozzle configured to direct the fluid in a plurality of discrete streams aligned in a radial fashion about an axis of the first lumen;
an interior catheter configured for placement within the first lumen, wherein a first end of the interior catheter includes an occluder and includes a first temperature sensor, the first temperature sensor configured to pass through the end orifice and the occluder configured to engage with the tapered interior wall in a fluid-tight seal;
wherein the first temperature sensor includes a sense surface and includes a signal node, wherein the signal node is configured to provide a first signal corresponding to a timewise change in temperature at the sense surface; and
wherein the interior catheter includes an upstream temperature sensor distal from the first end, and wherein an upstream signal from the upstream temperature sensor corresponds to a timewise change in temperature.

19. The system of claim 18 further including a guide wire configured to facilitate placement of the outer catheter, the guide wire configured to pass through the end orifice and the guide wire configured for extraction from the first lumen at the proximal end.

20. The system of claim 18 wherein the distal end of the outer catheter includes a balloon, the balloon configured for inflation by a second lumen, the second lumen having a first end coupled to an interior region of the balloon and having a second end proximate the proximal.

21. The system of claim 18 wherein the occluder includes an elastic portion.

22. The system of claim 18 wherein the discharge nozzle includes a plurality of apertures, wherein each aperture corresponds to a discrete stream.

23. The system of claim 22 wherein at least one aperture is aligned in a retrograde direction.

24. The system of claim 22 wherein at least one aperture is aligned in an antegrade direction.

25. The system of claim 22 wherein at least one aperture is aligned perpendicular to the axis.

26. A method of determining cardiac output comprising:
positioning a distal end of an outer catheter in a blood tract, the distal end having a discharge nozzle, a tapered interior wall, and an end orifice, the outer catheter having a proximal end configured to receive a fluid, the discharge nozzle coupled to the proximal end by a first lumen;
positioning an interior catheter in the first lumen, wherein a first end of the interior catheter includes an occluder and includes a first temperature sensor, the first temperature sensor configured to pass through the end orifice and the occluder configured to engage with the tapered interior wall in a fluid-tight seal;
introducing the fluid into the first lumen at the proximal end and discharging the fluid from the first lumen at the discharge nozzle, wherein discharging the fluid includes directing the fluid in a plurality of discrete streams aligned in a radial fashion about an axis of the first lumen;

receiving a first signal from the first temperature sensor, the first signal corresponding to a timewise change in temperature;

determining cardiac output using the first signal; and wherein positioning the interior catheter includes positioning an upstream temperature sensor distal from the first end, and further including receiving an upstream signal from the upstream temperature sensor, the upstream signal corresponding to a timewise change in temperature.

27. The method of claim 26 wherein positioning the distal end of the outer catheter includes passing the outer catheter over a guide wire.

28. The method of claim 26 further including extracting the guide wire from the first lumen at the proximal end.

29. The method of claim 26 wherein positioning the distal end of the outer catheter includes inflating a balloon and deflating the balloon, the balloon coupled to the distal end.

30. The method of claim 26 wherein positioning the interior catheter includes deforming an elastic portion of the occluder.

31. The method of claim 26 wherein discharging the fluid from the first lumen at the discharge nozzle includes discharging the fluid in a discrete stream aligned in a retrograde direction.

32. The method of claim 26 wherein discharging the fluid from the first lumen at the discharge nozzle includes discharging the fluid in a discrete stream aligned in an antegrade direction.

33. The method of claim 26 wherein discharging the fluid from the first lumen at the discharge nozzle includes discharging the fluid in a discrete stream aligned perpendicular to the axis.

34. The method of claim 26 wherein positioning the interior catheter includes advancing over a guidewire.

* * * * *